(12) United States Patent
Weiman et al.

(10) Patent No.: US 9,414,874 B2
(45) Date of Patent: Aug. 16, 2016

(54) LOW PROFILE FASTENING ASSEMBLY

(71) Applicant: GLOBUS MEDICAL, INC., Audubon, PA (US)

(72) Inventors: Mark Weiman, Coatesville, PA (US); Sean Suh, Morganville, NJ (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

(21) Appl. No.: 14/877,177

(22) Filed: Oct. 7, 2015

(65) Prior Publication Data

US 2016/0022338 A1   Jan. 28, 2016

Related U.S. Application Data

(60) Continuation of application No. 14/645,466, filed on Mar. 12, 2015, now Pat. No. 9,179,953, which is a division of application No. 14/103,556, filed on Dec. 11, 2013, now Pat. No. 9,005,258, which is a continuation of application No. 12/716,523, filed on Mar. 3, 2010, now Pat. No. 8,632,575.

(51) Int. Cl.
*A61B 17/04* (2006.01)
*A61B 17/86* (2006.01)
*A61F 2/08* (2006.01)
*A61B 17/88* (2006.01)

(52) U.S. Cl.
CPC ............... *A61B 17/861* (2013.01); *A61B 17/86* (2013.01); *A61B 17/8605* (2013.01); *A61B 17/88* (2013.01); *A61B 2017/8655* (2013.01)

(58) Field of Classification Search
None
See application file for complete search history.

(56) References Cited

U.S. PATENT DOCUMENTS

| | | | |
|---|---|---|---|
| 6,979,334 B2 | 12/2005 | Dalton | |
| 2005/0010218 A1* | 1/2005 | Dalton | ............... A61B 17/8023 606/304 |

* cited by examiner

Primary Examiner — Sameh Boles

(57) ABSTRACT

A fastener assembly that can be used for the fixation or anchoring of orthopedic devices or instruments to bone tissue. In particular, a low profile variable angle or fixed angle fastener assembly is able to securely connect the orthopedic device to bone tissue. The fastener assembly may have a locking mechanism that will quickly and easily lock the fastener assembly with respect to the orthopedic device.

18 Claims, 1 Drawing Sheet

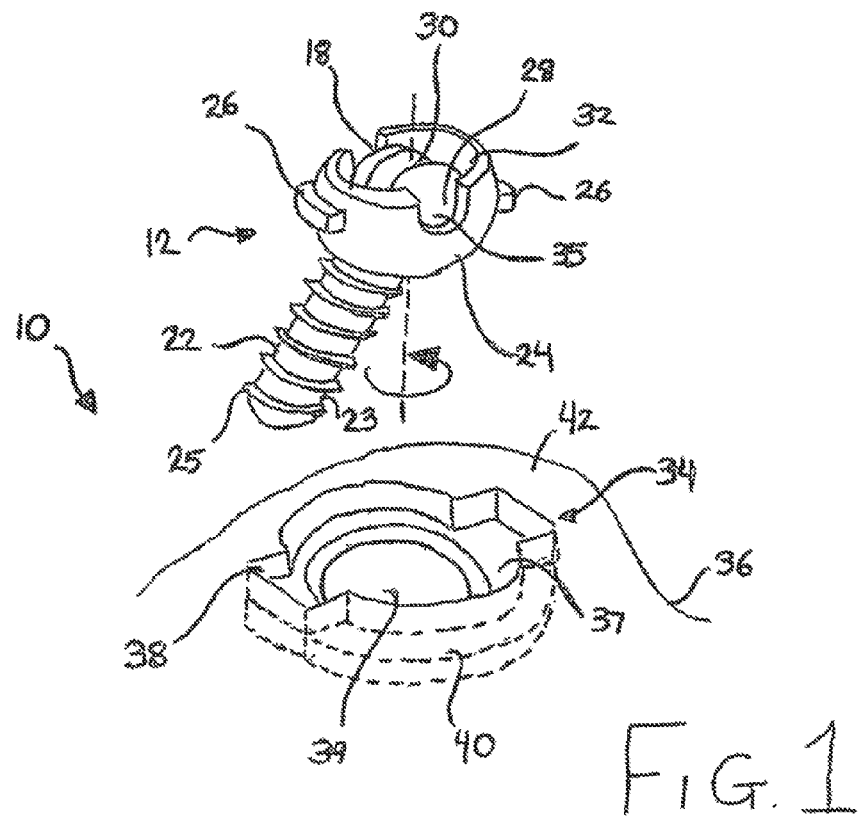
Fig. 1
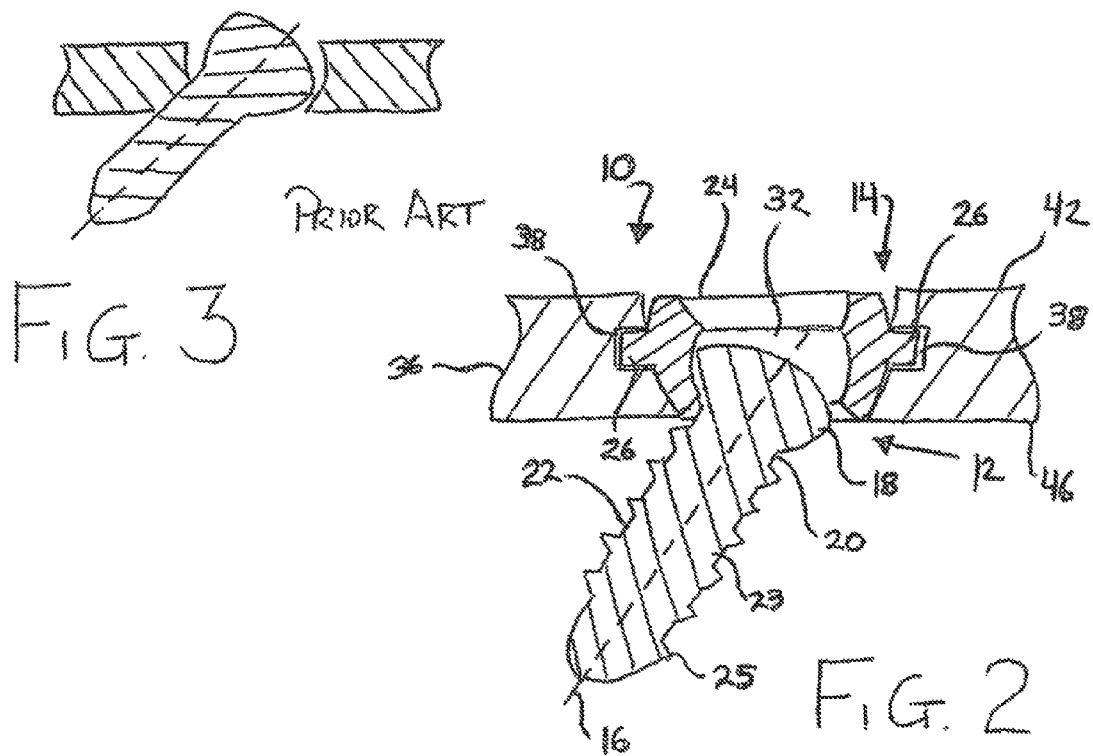
Fig. 3 PRIOR ART
Fig. 2

LOW PROFILE FASTENING ASSEMBLY

CROSS REFERENCE TO RELATED APPLICATIONS

This application is a continuation of U.S. patent application Ser. No. 14/645,466, filed Mar. 12, 2015, which is a divisional of U.S. patent application Ser. No. 14/103,556 filed on Dec. 11, 2013, now issued as U.S. Pat. No. 9,005,258, which is a continuation of U.S. patent application Ser. No. 12/716,523 filed on Mar. 3, 2010, now U.S. Pat. No. 8,632,575. The contents of these prior applications are hereby incorporated by reference in their entities for all purposes.

FIELD OF THE INVENTION

The present invention is directed to a bone fixation assembly and, in particular, to a low profile fastening assembly for securing an orthopedic device to bone tissue.

BACKGROUND OF THE INVENTION

As is known in the field of orthopedic surgery, and more specifically spinal surgery, orthopedic fasteners may be used for fixation or for the anchoring of orthopedic devices or instruments to bone tissue. An exemplary use of fasteners may include using the fastener to anchor an orthopedic device, such as a bone plate, a spinal rod or a spinal spacer to a vertebral body for the treatment of a deformity or defect in a patient's spine. Focusing on the bone plate example, fasteners can be secured to a number of vertebral bodies and a bone plate can be connected to the vertebral bodies via the bone anchors to fuse a segment of the spine. In another example, orthopedic fasteners can be used to fix the location of a spinal spacer once the spacer is implanted between adjacent vertebral bodies. In yet another example, fasteners can be anchored to a number of vertebral bodies to fasten a spinal rod in place along a spinal column to treat a spinal deformity.

However, the structure of spinal elements presents unique challenges to the use of orthopedic implants for supporting or immobilizing vertebral bodies. Among the challenges involved in supporting or fusing vertebral bodies is the effective installation of an orthopedic implant that will resist migration despite the rotational and translational forces placed upon the plate resulting from spinal loading and movement. Also, for certain implants, having low profile characteristics is beneficial in terms of patient comfort as well as anatomic compatibility.

Furthermore, over time, it has been found that as a result of the forces placed upon the orthopedic implants and fasteners resulting from the movement of the spine and/or bone deterioration, the orthopedic fasteners can begin to "back out" from their installed position eventually resulting in the fasteners disconnecting from the implant and the implant migrating from the area of treatment.

As such, there exists a need for a fastening system that provides for low profile placement of the bone anchor or screws and provides a mechanism where the fasteners are blocked to prevent the anchors from "backing out" of their installed position.

SUMMARY OF THE INVENTION

In a preferred embodiment, the present invention provides an anchor assembly that can be used for the fixation or fastening of orthopedic implants to bone tissue. In particular, the present invention preferably provides a low profile variable angle or fixed angle fastener assembly that is able to securely connect the orthopedic device to bone tissue. Furthermore, in a preferred embodiment, the present invention further provides a fastener assembly having a locking mechanism that will quickly and easily lock the anchor assembly with respect to the orthopedic device.

Further areas of applicability of the present invention will become apparent from the detailed description provided hereinafter. It should be understood that the detailed description and specific examples, while indicating the preferred or exemplary embodiments of the invention, are intended for purposes of illustration only' and are not intended to limit the scope of the invention.

BRIEF DESCRIPTION OF THE DRAWINGS

The present invention will become more fully understood from the detailed description and the accompanying drawings, wherein:

FIG. 1 is an exploded perspective view of one embodiment of a fastening assembly;

FIG. 2 is a cross sectional side view of the fastening assembly shown in FIG. 1; and FIG. 3 is schematic cross sectional side view of a prior art anchor system.

DETAILED DESCRIPTION OF THE INVENTION

The following description of the preferred embodiment(s) is merely exemplary in nature and is in no way intended to limit the invention, its application, or uses.

With reference to FIGS. 1 and 2, a preferred embodiment of a fastening assembly 10 is illustrated. The fastening assembly 10 preferably includes a fastener 12, a polyaxial locking head 24 and a locking mechanism 14. The fastening assembly 10 is preferably constructed from any biocompatible material including, but not limited to, stainless steel alloys, titanium, titanium based alloys, or polymeric materials. Although the fastener 12 will be discussed in the context of an orthopedic screw, it is contemplated that the fastener 12 can be any type of fastening element including, but not limited to, a hook, a pin, or a nail.

In a preferred embodiment, the fastener 12 includes, concentric to a longitudinal axis 16, a head portion 18, a neck portion 20 and a shank portion 22. The head portion 18 connects to the shank portion 22 through the neck portion 20. The neck portion 20 of the fastener 12, preferably, integrally connects the head portion 18 with the shank portion 22. The diameter of the neck portion 20 is preferably dimensioned to match a minor diameter of the fastener 12. By having the diameter of the neck portion 20 dimensioned at least as large as the minor diameter of the fastener 12, the overall rigidity and strength of the fastener 12 is increased.

In a preferred embodiment, the shank portion 22 of the fastener 12 includes a shaft 23 surrounded at least in part by a thread portion 25. The diameter of the shaft 23 is the minor diameter of the fastener 12. In a preferred embodiment, the diameter of the shaft 23 remains generally constant from a proximal end of the shaft 23 toward a distal end of the shaft 23. The constant diameter of a majority portion of the shaft 23 allows for optimal fastener positioning when the fastener 12 is inserted into a predetermined area in the bone tissue. The constant diameter also allows for varying the depth positioning of the fastener 12 in the bone. For example, if a surgeon places the fastener 12 into bone tissue at a first depth and decides the placement is more optimal at a second, shallower depth, the fastener 12 can be backed out to the second depth and still remain fixed in the bone. In another embodiment, the diameter of the shaft 23 may vary along its length, including increasing in diameter from the proximal end to the distal end or decreasing in diameter from the proximal end to the distal end.

With continued reference to FIGS. 1-2, the thread portion 25 surrounding the shaft 23 extends, in a preferred embodiment, from the distal end of the shaft 23 to the neck portion 20. In another preferred embodiment, the thread portion 25 may extend along only a portion of shaft 23. The thread portion 25 is preferably a Modified Buttress thread but the thread can be any other type of threading that is anatomically conforming, including, but not limited to Buttress, Acme, Unified, Whitworth and B&S Worm threads.

In a preferred embodiment, the diameter of the thread portion 25 decreases towards the distal end of the fastener 12. By having a decreased diameter thread portion 25 near the distal end of the fastener 12, the fastener 12 can be self-starting. In another preferred embodiment, fastener 12 may also include at least one flute to clear any chips, dust, or debris generated when the fastener 12 is implanted into bone tissue.

As best seen in FIG. 1, in a preferred embodiment, at least a portion of the head portion 18 of the fastener 12 has a generally spherical shape and is preferably surrounded by the polyaxial locking head 24. In another preferred embodiment, the polyaxial locking head 24 includes at least one extension 26, but, preferably includes two extensions 26; each extension 26 being located diametrically opposite to the other on the polyaxial locking head 24. Preferably, also located on polyaxial locking head 24 is at least one, but preferably two, notches or openings 28. The notches 28 are configured and dimensioned to correspond with the end of a driving instrument (not shown) designed to engage the polyaxial locking head 24. This engagement allows a user to manipulate the polyaxial locking head 24 through the driving instrument. Similarly, the head portion 18 of the fastener 12 also preferably includes a cavity or opening 30 configured and dimensioned to correspond with the end of the same driving instrument or a separate driving instrument (not shown) designed to engage the fastener 12. This engagement allows a user to drive the fastener 12 into bone tissue and otherwise manipulate the fastener 12.

Turning back to FIGS. 1 and 2, the generally spherical shape of the head portion 18 is configured and dimensioned to be received within a correspondingly shaped cavity 32 in the polyaxial locking head 24. The shape of the head portion 18 and the correspondingly shaped cavity 32 allows the fastener 12 to pivot, rotate and/or move with respect to the polyaxial locking head 24. It should be noted that the head portion 18 and the cavity 32 are dimensioned such that the head portion 18 cannot be removed or otherwise disengaged from the cavity 32 of the polyaxial locking head 24. In another embodiment, instead of allowing the fastener 12 to pivot, rotate and/or move with respect to the polyaxial locking head 24, the head portion 18 and the correspondingly shaped cavity 32 may be configured and dimensioned to keep the fastener 12 in a fixed position. In a preferred embodiment, the head portion 18 may include texturing 35 that extends along at least a portion of the head portion 18. The texturing 35 on the head portion 18 provides additional frictional surfaces which aid in gripping the fastener 12 and holding the fastener 12 in place with respect to the polyaxial locking head 24.

In an exemplary use with an orthopedic device, the fastener 12 with the polyaxial locking head 24 is received in an opening 34 in an orthopedic device 36. The opening is appropriately configured and dimensioned to receive the fastener 12 and the polyaxial locking head 24 such that the polyaxial locking head 24 can be rotated with respect to the device 36 and the fastener 12 can be pivoted, rotated or moved until the desired orientation is met with respect to the polyaxial locking head 24 and/or the device 36. In a preferred embodiment, the opening 34 includes an upper opening 37 which receives the polyaxial locking head 24 and the head portion 18 of the fastener 12 and a lower opening 39 which receives the shank portion 22. In a preferred embodiment, the upper opening 37 also includes extensions 38 which are configured and dimensioned to receive the extensions 26.

As mentioned above, in a preferred embodiment, the fastener assembly 10 includes the locking mechanism 14. The locking mechanism 14 will lock the fastener assembly 10 with respect to the orthopedic device 36 thereby preventing the fastener assembly 10 from disengaging or "backing out" from the orthopedic device 36. The locking mechanism 14 further assists in engaging the fastener 12 and the polyaxial locking head 24 with the opening 34 in the orthopedic device 36 in a low-profile arrangement. In a preferred embodiment, the locking mechanism 14 includes extensions 26 of the polyaxial locking head 24, corresponding extensions 38 in the opening 34, and grooves 40. In a preferred embodiment, the grooves 40 extend from one extension 38 to the other extension 38 and are generally radial. Preferably, the grooves 40 are located between the upper surface 42 and a lower surface 46 of the device 36.

In an exemplary use of the fastener assembly 10 with the orthopedic device 36, the orthopedic device 36 is first oriented and placed in the area of treatment. The orthopedic device 36 is then fastened to the bone tissue via at least one fastener assembly 10 which is received in at least one opening 34 of the orthopedic device 36. More specifically, looking at FIGS. 1-2, in a preferred embodiment, the fastener 12 and the polyaxial locking head 24 are received in opening 34 such that the shank portion 22 passes through the lower opening 39 and the polyaxial locking head 24 and head portion 18 are receiving and seated in the upper opening 37. The fastener 12 via notch 30 can then be driven into the bony tissue. As best seen in FIG. 2, when received in the opening 34, the polyaxial locking head 24 and the fastener 12 are received in a low profile manner. In other words, regardless of the position of fastener 12, even when the fastener 12 is rotated, pivoted, or otherwise moved, the head portion 18 of the fastener 12 will not breach the plane defined by an upper surface 42 of the device 36. This is in contrast to prior art systems, one of which is shown in FIG. 3, where the head of a fastener will breach the plane defined by the upper surface of the orthopedic implant. This is particularly true when the fastener is installed at a steep or sharp angle.

Once the fastener assembly 10 is seated in the cavity 34, the fastener assembly 10 can be locked in the opening 34 by actuating the locking mechanism 14. In a preferred embodiment, a user actuates locking mechanism 14 by rotating the polyaxial locking head 24 via notches 28 in a first direction. The rotational movement causes the extensions 26 which are seated in the extensions 38 to rotate into the grooves 40. Although only one groove is shown in broken lines in FIG. 1, it should be understood that there are two sets of diametrically opposed grooves 40 which extend in an annular fashion between the extensions 38. In a preferred embodiment, the grooves 40 include a stop to provide feedback to the user that the polyaxial locking head 24 has been fully rotated and the locking assembly 14 is engaged. In another preferred embodiment, the grooves 40 change in dimension so that the protrusions 26 can be captured in grooves 40 in an interference manner as the polyaxial locking head 24 is rotated. In yet another preferred embodiment, the grooves 40 include protrusions that provide audible and tactile feedback to the user as the user locks the fastening assembly 10.

With the polyaxial locking head 24 rotated, the fastener assembly 10 is locked in the opening 34 since the protrusion 26 in the grooves 40 prevents the polyaxial locking head 24 and fastener 12 from disengaging or "backing out" from the opening 34. If a user wants to unlock the locking mechanism 14 and remove fastener assembly 10 from the opening 34 of device 36, the user would simply rotate the polyaxial locking cap 24 via notches 28 in a second direction thereby rotating the protrusions 28 out of grooves 40 and into extensions 38. At that point the locking mechanism 14 is disengaged and the fastener assembly 10 can be removed from the opening 34 of the orthopedic device 36.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A surgical method comprising: inserting a bone plate into a patient, wherein the bone plate comprises an opening extending from an upper surface of the bone plate to a lower surface of the bone plate, wherein the bone plate comprises one or more grooves in communication with the opening; inserting a fastener assembly into the bone plate, wherein the fastener assembly comprises a locking head comprising an extension; and rotating the fastener assembly such that the extension is received in the one or more grooves of the bone plate to thereby prevent backout of the fastener assembly from the bone plate, wherein the locking head extending from most upper surface of the bone plate to most lower surface of the bone plate, and wherein the fastener assembly comprises a fastener including a head portion, a neck portion and a shank portion, wherein the head portion is received in an opening formed in the locking head.

2. The surgical method of claim 1, wherein the head portion of the fastener is received in an opening formed in the locking head.

3. The surgical method of claim 1, wherein the locking head comprises a second extension.

4. The surgical method of claim 1, wherein the extension extends from a spherical surface of the locking head.

5. The surgical method of claim 1, wherein the locking head comprises a pair of notches for receiving a driving instrument therein.

6. The surgical method of claim 1, wherein the head portion of the fastener is capable of pivoting and/or rotating relative to the locking head.

7. The surgical method of claim 1, wherein the locking head comprises a spherical opening formed therein.

8. The surgical method of claim 1, wherein the one or more grooves are radial.

9. The surgical method of claim 1, wherein the one or more grooves include a stop.

10. A surgical method comprising: inserting an orthopedic device into a patient, wherein the orthopedic device comprises an opening extending from an upper surface of the orthopedic device to a lower surface of the orthopedic device, wherein the orthopedic device comprises one or more grooves in communication with the opening; inserting a fastener assembly into the orthopedic device, wherein the fastener assembly comprises a locking head comprising a pair of extensions; and rotating the locking head such that the pair of extensions are received in the one or more grooves of the orthopedic device to thereby prevent backout of the fastener assembly from the orthopedic device, wherein the fastener assembly further comprises a fastener that is received in an opening of the locking head, and wherein the locking head extending from most upper surface of the orthopedic device to most lower surface of the orthopedic device.

11. The surgical method of claim 10, wherein the orthopedic device comprises a bone plate.

12. The surgical method of claim 11, wherein the one or more grooves are in communication with the opening.

13. The surgical method of claim 12, wherein the opening of the locking head is spherical.

14. The surgical method of claim 10, wherein the locking head comprises one or more notches for engaging a driving instrument.

15. The surgical method of claim 10, wherein the one or more grooves are radially formed.

16. The surgical method of claim 10, wherein the fastener assembly is retained within the orthopedic device such that an upper most surface of the fastener assembly remains below an upper most surface of the orthopedic device.

17. The surgical method of claim 10, wherein the orthopedic device comprises a plate.

18. The surgical method of claim 16, wherein the fastener is rotatable relative to the locking head.

* * * * *